(12) United States Patent
Zhao et al.

(10) Patent No.: US 10,444,130 B2
(45) Date of Patent: Oct. 15, 2019

(54) MATERIAL IN-SITU DETECTION DEVICE AND METHOD UNDER MULTI-LOAD AND MULTI-PHYSICAL FIELD COUPLED SERVICE CONDITIONS

(71) Applicant: JILIN UNIVERSITY, Changchun, Jilin (CN)

(72) Inventors: Hongwei Zhao, Jilin (CN); Shizhong Zhang, Jilin (CN); Luquan Ren, Jilin (CN); Ning Li, Jilin (CN); Xiaohang Dai, Jilin (CN); Shunbo Wang, Jilin (CN); Zhanwei Huo, Jilin (CN); Yang Liu, Jilin (CN); Daining Fang, Jilin (CN); Yongmao Pei, Jilin (CN)

(73) Assignee: JILIN UNIVERSITY, Changchun, Jilin (CN)

( * ) Notice: Subject to any disclaimer, the term of this patent is extended or adjusted under 35 U.S.C. 154(b) by 0 days.

(21) Appl. No.: 15/578,843

(22) PCT Filed: Sep. 24, 2015

(86) PCT No.: PCT/CN2015/090482
§ 371 (c)(1),
(2) Date: Dec. 1, 2017

(87) PCT Pub. No.: WO2017/012194
PCT Pub. Date: Jan. 26, 2017

(65) Prior Publication Data
US 2018/0180521 A1    Jun. 28, 2018

(30) Foreign Application Priority Data

Jul. 17, 2015  (CN) .......................... 2015 1 0422051

(51) Int. Cl.
*G01N 3/18* (2006.01)
*G01N 3/20* (2006.01)
(Continued)

(52) U.S. Cl.
CPC ................ *G01N 3/18* (2013.01); *G01N 3/068* (2013.01); *G01N 3/20* (2013.01); *G01N 3/22* (2013.01);
(Continued)

(58) Field of Classification Search
CPC ..................... G01N 3/18; G01N 3/068; G01N 3/20; G01N 3/22; G01N 3/42; G01N 2203/0026;
(Continued)

(56) References Cited

U.S. PATENT DOCUMENTS 8,978,480 B2    3/2015  Michopoulos et al.
9,835,217 B2 *  12/2017 Nakamura ................ F16F 1/04
(Continued)

FOREIGN PATENT DOCUMENTS

CN    103499308 A    1/2014
CN    103512803 A    1/2014
(Continued)

OTHER PUBLICATIONS

First Office Action issued by the State Intellectual Property Office of People's Republic of China dated Jun. 16, 2017 for related China Patent Application No. 201510422051.8.
(Continued)

*Primary Examiner* — Octavia Hollington
(74) *Attorney, Agent, or Firm* — Enshan Hong; VLP Law Group LLP (57) ABSTRACT

Provided are a material in-situ test device and method under multi-load and multi-physical field coupled service conditions. The device is composed of a precise six-degree-of-freedom composite load applying module, a precise torsion module, a precise indentation module, a clamp module and a control module which work together to complete a composite-load and multi-physical field coupled experiment, and is integrated with a digital speckle strain measurement and
(Continued)

infrared thermal imaging module and a microscope observation module, so as to carry out in-situ observation and quantitative characterization on material deformation behaviors and damage mechanism phenomena in a composite-load and multi-physical field loading process. For example, loading methods of "cantilever type pure bending, cantilever type tension/compression-torsion, and cantilever type bending-torsion", etc. can realize the loading of composite load. Silicon nitride ceramic heating sheets, Peltier tiles and current loading are used for achieving simulation of multiple physical fields such as cold/hot-electricity fields.

11 Claims, 8 Drawing Sheets

(51) Int. Cl.
  *G01N 3/22* (2006.01)
  *G01N 3/06* (2006.01)
  *G01N 3/42* (2006.01)
(52) U.S. Cl.
  CPC ....... *G01N 3/42* (2013.01); *G01N 2203/0026* (2013.01); *G01N 2203/0226* (2013.01); *G01N 2203/0441* (2013.01); *G01N 2203/0641* (2013.01); *G01N 2203/0647* (2013.01)
(58) Field of Classification Search
  CPC ... G01N 2203/0226; G01N 2203/0441; G01N 2203/0641; G01N 2203/0647; G01N 3/02
  USPC .......................................................... 73/800
  See application file for complete search history.

(56)  References Cited

U.S. PATENT DOCUMENTS

| | | | |
|---|---|---|---|
| 10,012,576 B2* | 7/2018 | Zhao | ........................ G01N 3/08 |
| 10,030,695 B2* | 7/2018 | Kurose | .................... B25J 18/06 |
| 2013/0055825 A1 | 3/2013 | Michopoulos et al. | |

FOREIGN PATENT DOCUMENTS

| | | |
|---|---|---|
| CN | 203551371 U | 4/2014 |
| CN | 203643255 U | 6/2014 |
| CN | 203643276 U | 6/2014 |
| CN | 104089815 A | 10/2014 |
| CN | 104677746 A | 6/2015 |

OTHER PUBLICATIONS

Second Office Action issued by the State Intellectual Property Office of People's Republic of China dated Sep. 21, 2017 for related China Patent Application No. 201510422051.8.

English translation of International Search Report and Written Opinion of the International Searching Authority dated Apr. 21, 2016 for related International Application No. PCT/CN2015/090482.

* cited by examiner

| Action of Single load | | | | | |
|---|---|---|---|---|---|
| Direction of load | Type of applied Load | | | | |
| | stretching | compress -ing | cantilever type bending | torsion | indentat -ion |
| X | | | $F_2/F_2'$ | | $F_5/F_5'$ |
| Y | | | $F_1/F_1'$ | | $F_4/F_4'$ |
| Z | $F_3$ | $F_3'$ | | $M_1$ | |

MATERIAL IN-SITU DETECTION DEVICE AND METHOD UNDER MULTI-LOAD AND MULTI-PHYSICAL FIELD COUPLED SERVICE CONDITIONS

CROSS-REFERENCE TO RELATED APPLICATIONS

This application is a Section 371 National Stage Application of International Application No. PCT/CN2015/090482, filed on Sep. 24, 2015 and entitled with "MATERIAL IN-SITU TEST DEVICE AND METHOD UNDER MULTI-LOAD AND MULTI-PHYSICAL FIELD COUPLED SERVICE CONDITIONS", which claims priority to Chinese Patent Application No. 201510422051.8, filed on Jul. 17, 2015 and entitled with "MATERIAL IN-SITU TEST DEVICE AND METHOD UNDER MULTI-LOAD AND MULTI-PHYSICAL FIELD COUPLED SERVICE CONDITIONS", the contents of which are incorporated herein by reference in their entirety.

FIELD OF THE DISCLOSURE

The present disclosure relates to a field of precise scientific instruments and, more particularly, to a material in-situ test device and method under multi-load and multi-physical field coupled service conditions. In addition to several types of the "tension/compression-torsion-bending-indentation" tests on the conventional testing machine, tests with novel loading methods such as "cantilever type pure bending, cantilever type tension/compression-torsion, cantilever type bending-torsion, and cantilever type tension/compression-bending-torsion", can be carried out under the action of a composite load. A multi-field and multi-load applying method is achieved by combining the loading of multi-physical fields such as cold/hot-electric fields at the same time. The strain of the test piece in the test process is measured with the new measurement method—non-contact digital speckle measurement technology.

DESCRIPTION OF THE RELATED ART

Manufacturing industry is a pillar industry of the national economy and shows national creativity, competitiveness and comprehensive national strength. The level of manufacturing industry is not only related to the people's production and life, but also related to the development of national defense, aviation and other fields, and even related to the country's sovereignty and security. It has proposed that among many factors that affect the level of material testing and detection, the lack of the test technology and equipment operating under conditions close to the service conditions is a bottleneck that restricts the development of new materials and the development of high-end equipment manufacturing industry. Therefore, developing a material testing equipment operating under conditions close to the service conditions will reasonably explain the material deformation behavior under the composite load multi-physical field loading process and the damage mechanism and prevent some of the loss caused by material damage in advance. Its economic and social benefits are immeasurable.

In the present research level, the material testing theoretical method and equipment are mature for a single load. However, these instruments and equipment can only impose a single load to evaluate the mechanical properties of the material, and cannot truly reflect the actual force state of the material. In the actual production and life, the material is generally subject to a superposition of a composite load and a multi-physical field, which shows mechanical properties that are more complicated than that upon applying a single load. Therefore, the single function of the test instrument seriously restricts the development of the micro-test technology, and it is necessary to develop a micro-performance in-situ test device for the composite load multi-physics field coupling material.

SUMMARY OF THE INVENTION

The object of the present disclosure is achieved through the following technical solution:

The material in-situ test device under multi-load and multi-physical field coupled service conditions, in which a vertical asymmetric arrangement with three columns is adopted, and the device includes a support frame module 1, a shock isolation platform 2, a precise six-degree-of-freedom composite load applying module 3, a precise torsion module 4, a clamp and electrothermal coupling module 5, a digital speckle strain measurement and infrared thermal imaging module 6, an in-situ observation module 7, a precise indentation module 8 and a circumferential positioning module 9. The precise six-degree-of-freedom composite load applying module 3 is connected to the support frame module 1 by a stationary platform 15. The loading of tension/compression and bending loads on the test piece is achieved by means of the cooperation action of six electric cylinders 14. The precise torsion module 4 is provided on a movable platform 10 of the precise six-degree-of-freedom composite load applying module 3. The clamp and electrothermal coupling module 5 is connected to the precise torsion module 4 via a flange. The digital speckle strain measurement and infrared thermal imaging module 6 is provided on the shock isolation platform 2 through an adjustable support base 87. The in-situ observation module 7 and the precise indentation module 8 are provided on the circumferential positioning module 9 to realize a rotatable in-situ observation on the test piece.

BRIEF DESCRIPTION OF THE DRAWINGS

The drawings described herein are intended to provide a further understanding to the disclosure and constitute a part of this application. The illustrative embodiments and the description thereof are intended to explain the disclosure and not to be construed as a limiting to the disclosure.

NUMERAL SIGNS 1 support frame module;
2 shock isolation platform;
3 precise six-degree-of-freedom composite load applying module;
4 precise torsion module;
5 clamp and electrothermal coupling module;
6 digital speckle strain measurement and infrared heat imaging module;
7 in-situ observation module;
8 precise indentation module;
9 circumferential positioning module;
10 movable platform;
11 Hooke hinge;
12 motor;
13 decelerator;
14 electric cylinder;
15 stationary platform;
16 sensor flange;
17 first fixing base;
18 bearing baffle;
19 spline shaft;
20 DC servo drive motor;
21 planetary gear reducer;
22 end cover;
23 first thrust bearing;
24 second thrust bearing;
25 flange;
26 six-dimensional force sensor;
27 micromotion universal ball;
28 test piece;
29 first baffle;
30 pre-load bolt;
31 cover plate;
32 silicon nitride ceramic heating sheet;
33 connecting cooling base;
34 double end stud;
35 first sealing gasket;
36 nut;
37 heat insulation plate;
38 second sealing gasket;
39 insulated heat insulation plate;
40 bolt;
41 cable copper nose;
42 clamp body;
43 pin;
44 first servo motor;
45 coupling;
46 first support base;
47 mobile platform;
48 flexible hinge;
49 piezoelectric ceramic;
50 fixing plate;
51 micromotion platform;
52 weighing sensor;
53 displacement sensor;
54 second baffle;
55 indenter fixing sleeve;
56 indenter;
57 first screw;
58 second support base;
59 second fixing base;
60 first slider;
61 first guide rail;
62 sensor holder;
63 proximity switch;
64 motor fixing plate;
65 circular guide rail;
66 support disk;
67 circular ring gear;
68 second servo motor;
69 speed reducer;
70 observation platform;
71 roller;
72 microscope;
73 connecting plate;
74 second slider;
75 nut pair;
76 second screw;
77 third servo motor;
78 movable connection plate;
79 stepping motor;
80 second guide rail;
81 third slider;
82 third screw;
83 fourth slider;
84 infrared thermal imager;
85 third support base;
86 digital speckle measuring head;
87 adjustable support base;
88 indentation assembly;
89 motor screw nut pair assembly.

DETAILED DESCRIPTION OF EMBODIMENTS

The details and the specific embodiments of the present disclosure will be further described with reference to the accompanying drawings.

An object of the present disclosure is to provide a material in-situ test device and method under multi-load and multi-physical field coupled service conditions so as to solve the problem that a compound load applying cannot be realized in the existing test technology. In addition to several types of the "tension/compression-torsion-bending-indentation" tests on the conventional testing machine, tests with novel loading methods of "cantilever type pure bending, cantilever type tension/compression-torsion, cantilever type bending-torsion, and cantilever type tension/compression-bending-torsion", etc. can be carried out under the action of a composite load. At the same time combined with the loading of cold/hot-electric and other multi-physical fields, a multi-field and multi-load applying method is achieved. The strain of the test piece in the test process is measured with the new measurement method—non-contact digital speckle measurement technology. It provides an important test method for developing inherent relation between topography of microstructure of the material and its macroscopic mechanical properties under a condition close to the service condition.

Figure 1:
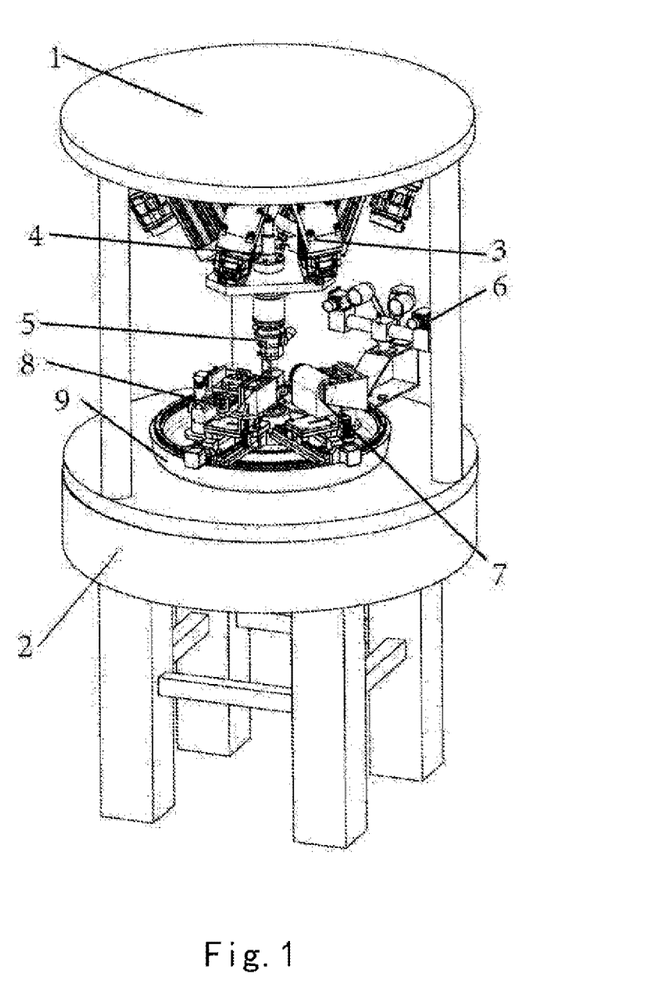
FIG. 1 is a schematic view of the overall structure of the device according to the present disclosure.
Figure 2:
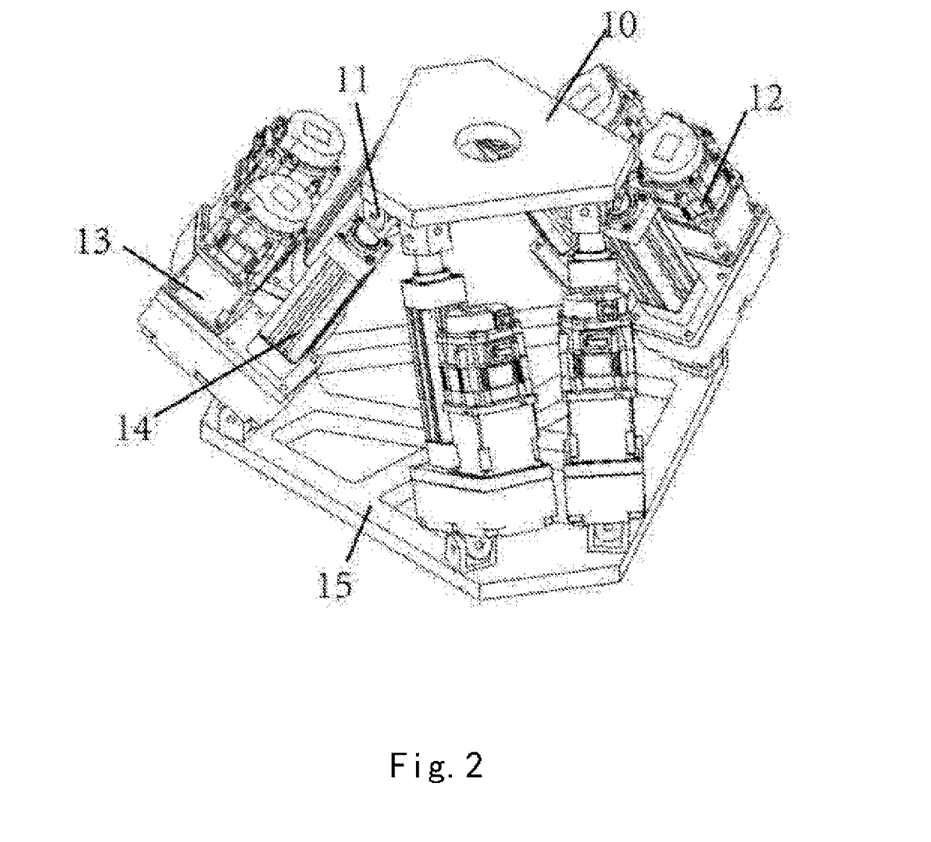
FIG. 2 is a schematic view of the various parts of the precise six-degree-of-freedom composite load applying module according to the present disclosure.

The precise six-degree-of-freedom composite load applying module 3 includes a movable platform 10, a Hooke hinge 11, a motor 12, a decelerator 13, electric cylinders 14 and a stationary platform 15. The stationary platform 15 is fixedly connected to the support frame module 1. One end of each electric cylinder 14 is connected to the movable platform 10 through the Hooke hinge 11 and the other end is connected to the stationary platform 15. The motor 12 and the decelerator 13 are connected to the stationary platform 15, respectively. Under the cooperation action of the six electric cylinders 14, a flexible movement in six degrees of freedom can be achieved.

Figure 3:
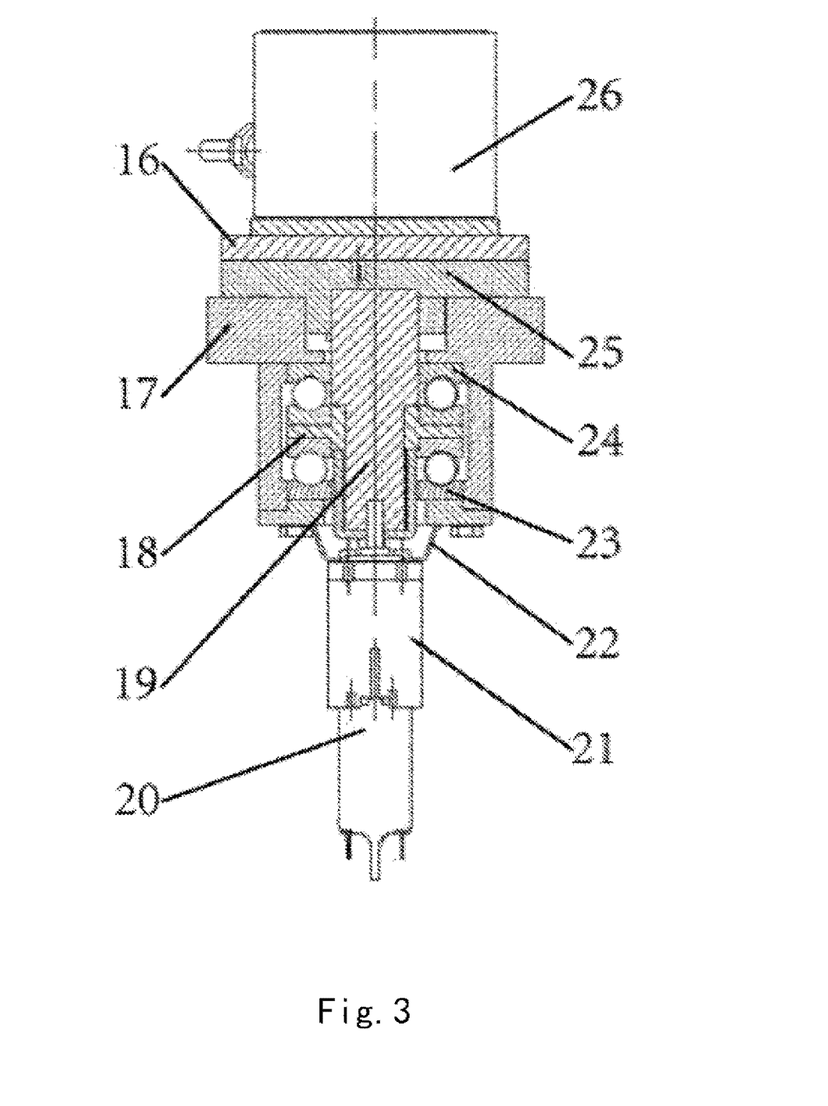
FIG. 3 and FIG. 4 are schematic views of the various parts of the precise torsion module according to the present disclosure.
Figure 4:
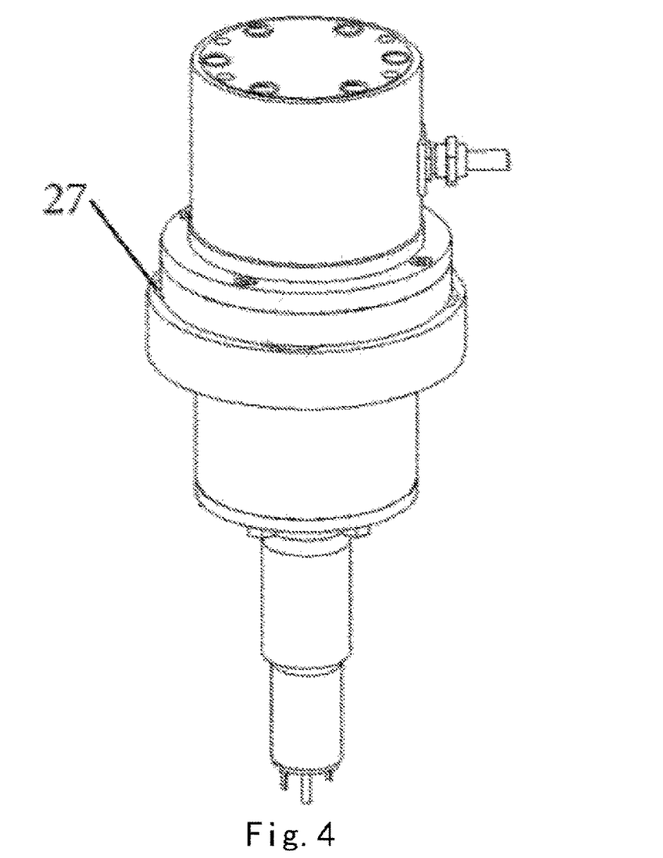

The torsional feed in the precise torsion module 4 is provided by a DC servo drive motor 20 and a planetary gear reducer 21. A first thrust bearing 23 and a second thrust bearing 24 are mounted on a spline shaft 19 to counteract an axial load generated on the DC servo drive motor 20 and the planetary gear reducer 21 when a tension/compression load is loaded; the spline shaft 19 transmits the torque to the flange 25 by a spline; the shaft end of the spline shaft 19 is bolted to the flange 25 and transmits the axial tension/compression force.

Figure 5:
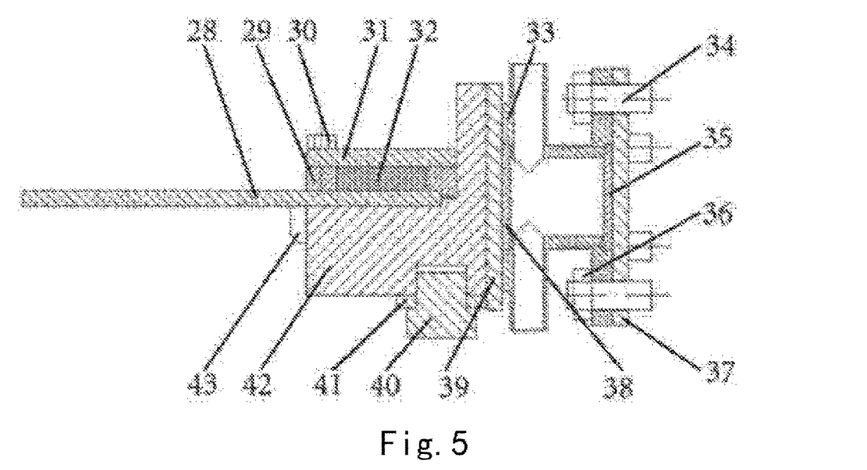
FIG. 5 is a cross-sectional view of various parts of the clamp and electrothermal coupling module according to the present disclosure.

The clamp and electrothermal coupling module 5 is connected to a six-dimensional force sensor 26 by means of two double end studs 34. The test piece is clamped by tightening a pre-load bolt 30 to produce a downward compression force to compress a cover plate 31 and a first baffle 29. The test piece is tightly pressed by means of the friction force via a groove in the clamp that matches the test piece in shape.

The clamp and electrothermal coupling module 5 integrates the clamp with the function of loading the cold, hot and electric multi-physical fields. The loading of the hot field is achieved by energizing a silicon nitride ceramic heating sheet 32 provided in the clamp in advance to load the heat field. The loading of the cold field is achieved by replacing the silicon nitride ceramic heating sheet 32 with a Peltier patch and energizing the Peltier patch, thereby achieving the refrigerating. The loading of the electric field is achieved by connecting a wire to a cable copper nose 41 and loading the current.

Figure 8:
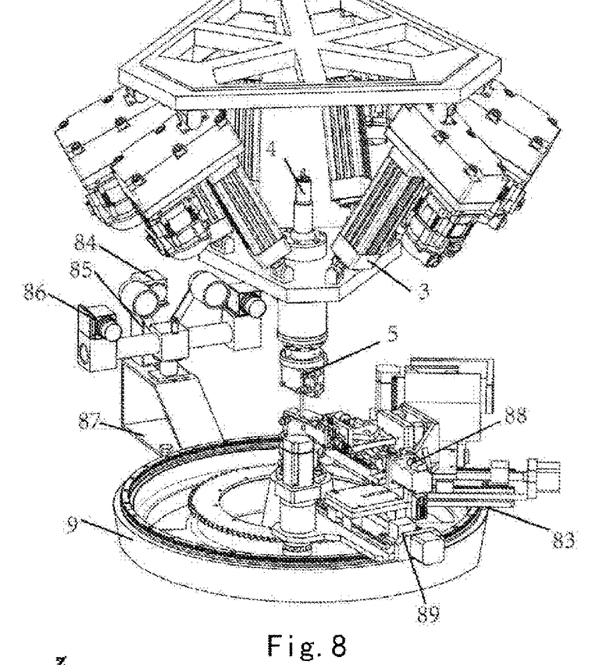
FIG. 8 is a schematic view showing an arrangement of the test execution mechanism according to the present disclosure.

In the digital speckle strain measurement and infrared thermal imaging module 6, a digital speckle measuring head 86 is provided on the shock isolation platform 2 through an adjustable support base 87. An infrared thermal imager 84 is fixed to a third support base 85, and the third support base 85 is fixed to the adjustable support base 87. The position of the adjustable support base 87 relative to the test piece 28 can be adjusted to meet the desired parameter requirements for the operation of the digital speckle measuring head 86.

Figure 7:
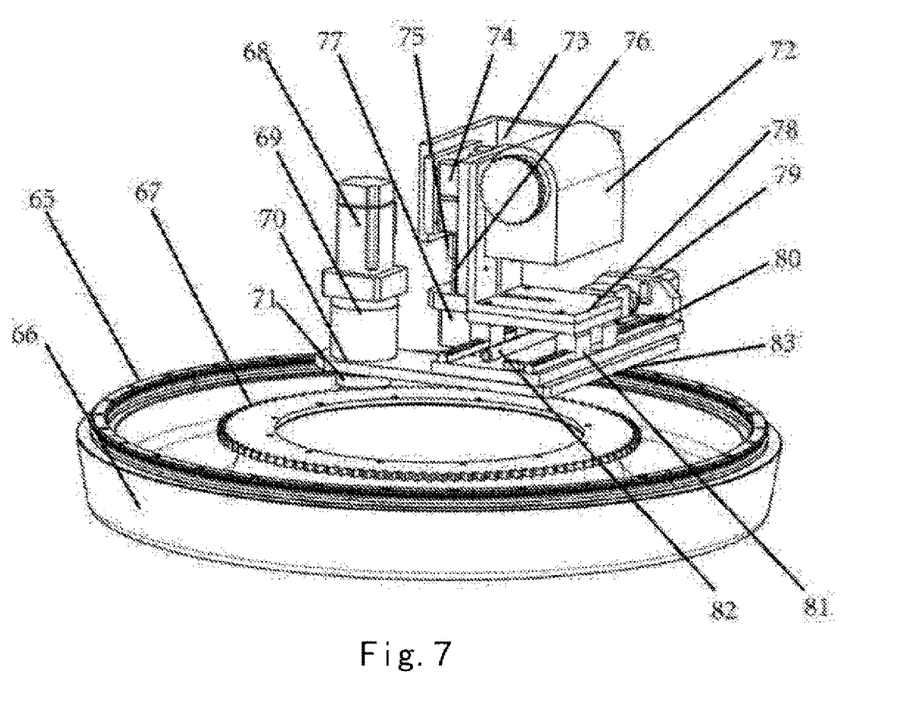
FIG. 7 is a schematic view of the various parts of the in-situ observation module according to the present disclosure.

The in-situ observation module 7 is entirely fixed to the observation platform 70, and the observation platform 70 is circumferentially rotated about the test piece 28. When the observation platform 70 is intended to be driven, a second servo motor 68 and a speed reducer 69 drive a roller 71 to rotate, and the roller 71 engages with a circular ring gear 67 to achieve a circumferential feed, and the whole observation platform 70 is fixed to a fourth slider 83, thereby achieving a circumferential motion.

The radial and axial rapid feed of the in-situ observation module 7 around the circular ring gear 67 is realized by a stepping motor 79 and a servo motor 77, respectively. A microscope 72 is rapidly moved into the observation area, and then the microscope 72 is automatically focused. After the focus is adjusted as desired, the observation is carried out.

Figure 6:
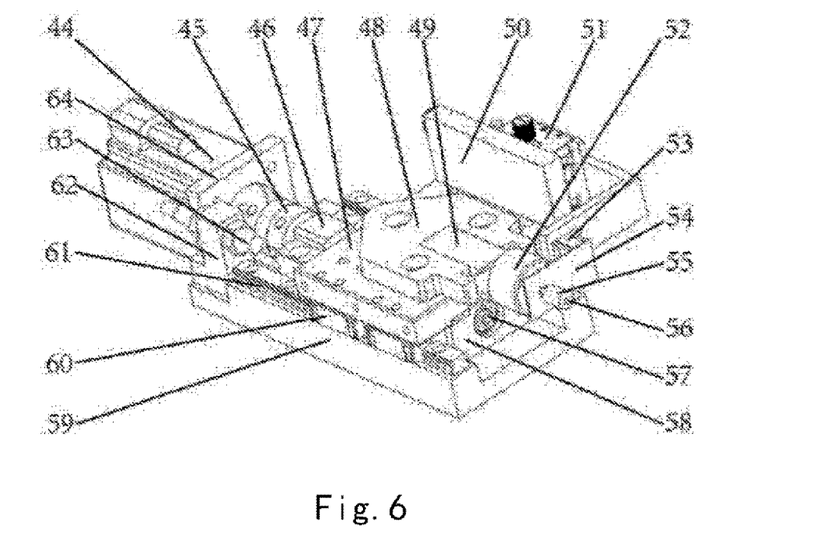
FIG. 6 is a schematic view of the various parts of the precise indentation module according to the present disclosure.

The precise indentation module 8 is fixed to the circumferential positioning module 9. When the precise indentation module 8 operates, the radial and axial rapid feed of the precise indentation module 8 around the circular ring gear 67 is carried out by two ball screw drive units. After the positioning is completed, a flexible hinge 48 is driven by means of a piezoelectric ceramic 49 to produce a forward displacement, thereby pressing an indenter 56 into the test piece.

Another object of the present disclosure is to provide a material in-situ testing method under multi-load and multi-physical field coupled service conditions, particularly including the following steps:

Step 1: applying a tension/compression load borne by a test piece 28 by means of a precise six-degree-of-freedom composite load applying module 3, wherein each electric cylinder 14 is driven to elongate or shorten by a motor 12 and a decelerator 13 that are connected to a stationary platform 15, the load is transferred from a movable platform 10 to a precise torsion module 4 and then from the precise torsion module 4 to a clamp and electrothermal coupling module 5, thereby achieving the loading of the tension/compression load on the test piece 28;

Step 2: applying a torsion load borne by the test piece 28 by means of the precise torsion module 4, wherein a DC servo drive motor 20 and a planetary gear reducer 21 drive a spline shaft 19 to rotate, and the spline shaft 19 drives a sensor flange 16, a flange 25 and a six-dimensional force sensor 26 to rotate, thereby rotating the upper end of a clamp and electrothermal coupling module 5 and realizing the loading of the torsion load on the test piece 28 with the lower end of the clamp and electrothermal coupling module 5 being fixed;

Step 3: applying a cantilever bending load borne by the test piece 28 by means of the precise six-degree-of-freedom composite load applying module 3, wherein the six electric cylinders 14 are driven to elongate or shorten to different extents by the motor 12 and the decelerator 13 that are connected to the stationary platform 15, the load is transferred from the movable platform 10 to the precise torsion module 4 and then from the precise torsion module 4 to the clamp and electrothermal coupling module 5, and the trajectory route of the test piece 28 in moving under the action of cantilever bending moment is simulated, thereby achieving the loading of the cantilever bending load on the test piece 28;

Step 4: carrying out an indentation test nondestructive detection of the test piece 28 through a precise indentation module 8, where in operation, a rapid feed in horizontal and vertical directions is firstly performed by two ball screw drive units, then a first servo motor 44 drives a first screw 57 via a coupling 45 to move a mobile platform 47 to realize the precise feed and finally, a flexible hinge 48 is driven by a piezoelectric ceramic 49 to push a weighing sensor 52 and an indenter 56 forward so as to press the indenter into the test piece, wherein the displacement distance of a second baffle 54 is measured by a displacement sensor 53, and the pressing depth can be measured indirectly, and wherein a plurality of types of loads are applied in combination to constitute a multi-load applying mode, and the strain generated in the test piece 28 in the testing process can be obtained through a digital speckle measuring head 86;

Step 5: loading a hot field on the test piece 28 by applying different operating voltages to a silicon nitride ceramic heating sheet 32 in the clamp and electrothermal coupling module 5 and by heating the test piece 28 to different temperatures in a heat conductive manner, wherein the temperature is measured by a infrared thermal imager 84;

Step 6: loading a cold field on the test piece 28 by replacing the silicon nitride ceramic heating sheet 32 for heating in loading the hot field with a Peltier patch to refrigerate the test piece 28 to different temperatures, wherein the temperature is measured by the infrared thermal imager 84;

Step 7: loading an electric field on the test piece 28 in a manner of loading a large current, wherein the electric field is loaded by connecting the wire to a cable copper nose 41 and outputting a large current, and wherein the material performance detection test under the multi-load and multi-physical field test conditions is realized by combining the loading of the multi physical fields and the loading of multi loads.

The disclosure has the following advantages.

1. The structure is novel and the layout is compact. The applying of the composite load according to the present disclosure is mainly achieved by the precise six-degree-of-freedom composite load applying module and the precise torsion module. In addition to the individually loading the conventional four types of loads, i.e. "tension/compression-torsion-bending-indentation", the loading of a composite load can also be achieved, such as "cantilever type pure bending, cantilever type tension/compression-torsion, cantilever type bending-torsion, cantilever type tension/compression-bending-torsion" and other new loading method. The real simulation on the state of stress in material is performed under a condition close to the service condition of the material.

2. The device is generally designed with modular design in which a support frame module, a shock isolation platform, a precise six-degree-of-freedom composite load applying module, a precise torsion module, a clamp and electrothermal coupling module, a digital speckle strain measurement and infrared thermal imaging module, an in-situ observation module, a precise indentation module, a circumferential positioning module are included. Thereby the device can be standardized and is easy for maintenance.

3. The precise torsion module of the device structurally adopts a double thrust ball bearing structure to cancel the large impact force on the DC servo drive motor and the planetary gear reducer when the axial large load is tensed/compressed. The module also uses several micromotion universal balls, and in the large load compression—torsion test, the micromotion-universal balls between engaging surfaces can convert the sliding friction into rolling friction when the material is twisted, so as to reduce the impact of friction on the torsion.

4. The device provides a circumferential surrounding observation mode. The microscope can be circumferentially rotated around the axis of the test piece in the observation process by means of the integrated microscope, so that the deformation of microstructure in various directions in micro-deformation process of the observed material can be observed more comprehensively.

5. The clamp of the device is integrated with the function of loading cold/hot, electric and other multi-physical fields. By placing a silicon nitride ceramic heating sheet or a Peltier patch in the clamp, the test piece can be heated or cooled to effect the loading of the cold or hot field. The wire connected to the exterior is connected to the cable copper nose and the electric field is loaded in a manner of loading current.

6. The device adopts a novel non-contact optical strain measurement—digital speckle technology. By using this technique, the overall strain of the test piece under the coupling of the composite load of the multi-physics fields can be dynamically measured, showing the strain amplitude at any position and the position of the stress and strain concentration.

7. The temperature of the device is controlled by using the infrared thermal imaging technology, so that the overall temperature distribution can be seen directly through the display screen. At the same time, the collected temperature value is fed back to the host computer and compared with the set temperature, thereby achieving a closed-loop feedback control.

Referring to FIGS. 1 to 8, the material in-situ test device under multi-load and multi-physical field coupled service conditions according to the disclosure includes a support frame module 1, a shock isolation platform 2, a precise six-degree-of-freedom composite load applying module 3, a precise torsion module 4, a clamp and electrothermal coupling module 5, a digital speckle strain measurement and infrared thermal imaging module 6, an in-situ observation module 7, a precise indentation module 8 and a circumferential positioning module 9. In the device according to the disclosure, a vertical asymmetric arrangement with three columns is adopted. The precise six-degree-of-freedom composite load applying module 3 is connected to the support frame module 1 by a stationary platform 15 of the precise six-degree-of-freedom composite load applying module 3. The loading of tension/compression and bending loads in the device is achieved by means of the cooperation action of the six electric cylinders 14. The precise torsion module 4 is provided on a movable platform 10 of the precise six-degree-of-freedom composite load applying module 3. The clamp and electrothermal coupling module 5 is connected to the precise torsion module 4 via a flange. The digital speckle strain measurement and infrared thermal imaging module 6 is provided on the shock isolation platform 2 through an adjustable support base 87. The in-situ observation module 7 and the precise indentation module 8 are provided on the circumferential positioning module 9 to realize a rotatable in-situ observation on the test piece. In addition to the loading method of the conventional four types of loads, i.e. "tension/compression-torsion-bending-indentation", a composite load can also be applied. That is, by simultaneously coupling the temperature field and the electric field, a material in-situ performance test under "machine-electric-heat" composite load multi-physical field coupling conditions can be carried out.

Referring to FIG. 2, the precise six-degree-of-freedom composite load applying module 3 according to the present disclosure is mainly implemented by a precise six-degree-of-freedom platform. The precise six-degree-of-freedom platform is mainly composed of a movable platform 10, a Hooke hinge 11, a motor 12, a decelerator 13, an electric cylinder 14, a stationary platform 15 and six electric cylinders 14. The stationary platform 15 is fixed to the support frame module 1 by bolts. In operation, the host computer software sends instructions, and after receiving the instructions, the platform control software converts the instructions into control parameters to drive the six electric cylinders 14 to synergistically act. The platform is mainly used to apply tension/compression and bending loads and a combination of several types of loads.

Referring to FIGS. 3 and 4, the precise torsion module 4 according to the present disclosure is mainly composed of a sensor flange 16, a first fixing base 17, a bearing baffle 18, a spline shaft 19, a DC servo drive motor 20, a planetary gear reducer 21, an end cover 22, a first thrust bearing 23, a second thrust bearing 24, a flange 25, a six-dimensional force sensor 26, and micromotion universal balls 27. The DC servo drive motor 20 is connected to the planetary gear reducer 21, and the planetary gear reducer 21 is fixed to the end cover 22 which is fixed to the first fixing base 17 by bolts. The planetary gear reducer 21 and the spline shaft 19 are connected by a spline connection. The support portion supporting the spline shaft 19 is constituted by a first thrust bearing 23, a bearing baffle 18, and a second thrust bearing 24, and the entire support portion is arranged inside the first fixing base 17 which is fixed to the movable platform 10 by bolts. The spline shaft 19 is bolted to the flange 25 which transmits the torque by means of the spline, and the sensor flange 16 and the flange 25 are bolted. The six-dimensional force sensor 26 is bolted to the sensor flange 16, and the micromotion universal balls 27 are provided at the engagement surface between the flange 25 and the first fixing base 17. When the precise torque module is operated, with the deceleration effect of the planetary gear reducer 21, the DC servo drive motor 20 outputs the torque to drive the spline shaft 19 to rotate. The spline shaft 19 transmits the torque to the six-dimensional force sensor 26 via the sensor flange 16 and the flange 25 and then to the clamp and the test piece.

Referring to FIG. 5, the clamp and electrothermal coupling module 5 according to the present disclosure mainly includes three functions: a clamp function, a cold/hot field loading function, and an electric field loading function. The clamp and electrothermal coupling module 5 includes a first baffle 29, a pre-load bolt 30, a cover plate 31, a silicon nitride ceramic heating sheet 32, a connecting cooling base 33, a double end stud 36, a first sealing gasket 35, a nut 36, a heat insulation plate 37, a second sealing gasket 38, an insulated heat insulation plate 39, a bolt 40, a cable copper nose 41, a clamp body 42, a pin 43. The first baffle 29, the cover plate 31 and the clamp body 42 are connected together by a pre-load bolt 30. The silicon nitride ceramic heating sheet 32 is tightly pressed by the cover plate 31, and the bolt 40 fixes the cable copper nose 41 to the clamp body 42. The pin 43 engages with the clamp body 42 in an interference fit. The connecting cooling base 33, the insulated heat insulation plate 39 and the clamp body 42 are connected by bolts. The second sealing gasket 38 engages with the connecting cooling base 33 in an interference fit. The first sealing gasket 35 engages with the connecting cooling base 33 in an interference fit. The double end stud 34, the nut 36 connects the connecting cooling base 33 and the heat insulation plate 37 to the following sensor. The loading of the thermal field is achieved by heating the silicon nitride ceramic heating sheet 32 provided in the clamp in advance to load the heat field in a heat conductive manner. The loading of the cold field is achieved by replacing the silicon nitride ceramic heating sheet 32 with a Peltier patch, thereby realizing the refrigerating in a cold conductive manner. The loading of the electric field is achieved by connecting the electric wire to the cable copper nose 41 and loading a large current.

Referring to FIG. 6, the precise indentation module 8 according to the present disclosure is mainly used for indentation testing (nondestructive detection). The precise indentation module 8 includes a first servo motor 44, a coupling 45, a first support base 46, a mobile platform 47, a flexible hinge 48, a piezoelectric ceramic 49, a fixing plate 50, a micromotion platform 51, a weighing sensor 52, a displacement sensor 53, a second baffle 54, a indenter fixing sleeve 55, a indenter 56, a first screw 57, a second support base 58, a second fixing base 59, a first slider 60, a first guide rail 61, a sensor holder 62, a proximity switch 63, and a motor fixing plate 64. The first servo motor 44 is fixed by the motor fixing plate 64 and is connected to the first screw 57 fixed to the first support base 46 and the second support base 58 via the coupling 45. The first support base 46 and the second support base 58 are bolted to the second fixing base 59. The first slider 60 is fitted with the first guide rail 61 together and is fixed to the second fixing base 59 by means of inner hexagonal bolt. The proximity switch 63 is fixed to the second fixing base 59 by means of inner hexagonal bolt via the sensor holder 62. The indenter 56 is fixed to the weighing sensor 52 by means of an indenter fixing sleeve 55 and the second baffle 54. The weighing sensor 52 is connected to the flexible hinge 48. The piezoelectric ceramic 49 is mounted inside the flexible hinge 48 and the flexible hinge 48 is mounted on the mobile platform 47. The distance between the displacement sensor 53 and the second baffle 54 may provide accurate feed of a displacement by means of a micromotion platform 51 fixed to the fixing plate 50. All these components form an indentation execution unit which is entirely arranged on a ball screw unit. The ball screw unit is used to achieve a rough positioning in the indentation feed.

Referring to FIG. 7, the in-situ observation module 7 according to the present disclosure is mainly composed of a circular guide rail 65, a support disk 66, a circular ring gear 67, a second servo motor 68, a speed reducer 69, an observation platform 70, a roller 71, a microscope 72, a connecting plate 73, a second slider 74, a nut pair 75, a second screw 76, a third servo motor 77, a movable connection plate 78, a stepping motor 79, a second guide rail 80, a third slider 81, a third screw 82, and a fourth slider 83. The support disk 66 is fixed to the shock isolation platform 2 by bolts; the microscope 72 is fixed to the connecting plate 73, and the connection plate 73 is mounted to the second slider 74 by bolts. The second slider 74, the nut pair 75, the second screw 76, the third servo motor 77 constitute a longitudinal feed mechanism which can adjust the longitudinal displacement of the microscope. The microscope 72 and the longitudinal feed mechanism are connected to the movable connection plate 78. The stepping motor 79 outputs the torque to the third screw 82 via the coupling. The movable connection plate 78 is arranged on the slide unit composed of the third slider 81 and the second guide rail 80 by the inner hexagon bolt(s) and is driven to move by the third screw 82. The in-situ observation module 7 is entirely arranged on a radial feed mechanism consisting of the stepping motor 79, the second guide rail 80, the third slider 81, and the third screw 82. The prominent feature of the in-situ observation module is the ability to achieve a circumferential observation. Therefore, in the present disclosure, all of the above-described components are placed on the observation platform 70. The second servo motor 68 and the speed reducer 69 drive the roller 71, and the roller 71 is engaged with the circular ring gear 67 to realize a circumferential motion. At the same time, the observation platform 70 are bolted to the fourth slider 83 fixed to the circular guide rail 65 so as to counteract the overturning moment generated during the movement of the observation mechanism.

Referring to FIG. 8, the test actuator arrangement according to the present disclosure includes the precise six-degree-of-freedom composite load applying module 3, the precise torsion module 4, the clamp and electrothermal coupling module 5, the digital speckle strain measurement and infrared thermal imaging module 6, the in-situ observation module 7, the precise indentation module 8, and the circumferential positioning module 9. The digital speckle measuring head 86 in the digital speckle strain measurement and infrared thermal imaging module 6 is arranged on the shock isolation platform 2 by means of an adjustable fixing bracket 87. The infrared thermal imager 84 is fixed to the third support base 85. The third support base 85 is fixed to the adjustable fixing bracket 87. The position of the fixing bracket 87 with respect to the test piece 28 can be adjusted to ensure the required work distance of the digital speckle measuring head 86. The precise indentation module 8 is mounted on a same mobile platform in the in-situ observation module 7 in which axial feed and radial feeds can be respectively and simultaneously realized. The indentation assembly 88 is connected to the motor screw nut pair 89 via inner hexagonal bolt(s).

Referring to FIGS. 1 to 13, the material in-situ test method under multi-load and multi-physical field coupled service conditions includes the following steps:

Step 1: applying a tension/compression load borne by a test piece 28 by means of a precise six-degree-of-freedom composite load applying module 3, wherein an electric cylinder 14 is driven to elongate or shorten by a motor 12 and a decelerator 13 that are connected to a stationary platform 15, the load is transferred from a movable platform 10 to a precise torsion module 4 and then from the precise torsion module 4 to a clamp and electrothermal coupling module 5, thereby applying the tension/compression load on the test piece 28;

Step 2: applying a torsion load borne by the test piece 28 by means of the precise torsion module 4, wherein a DC servo drive motor 20 and a planetary gear reducer 21 drive a spline shaft 19 to rotate, and the spline shaft 19 drives a sensor flange 16, a flange 25 and a six-dimensional force sensor 26 to rotate, thereby rotating the upper end of a clamp and electrothermal coupling module 5 and applying the torsion load on the test piece 28 with the lower end of the clamp and electrothermal coupling module 5 being fixed;

Step 3: applying a cantilever bending load borne by the test piece 28 by means of the precise six-degree-of-freedom composite load applying module 3, wherein the six electric cylinders 14 are driven to elongate or shorten to different extents by the motor 12 and the decelerator 13 that are connected to the stationary platform 15, the load is transferred from the movable platform 10 to the precise torsion module 4 and then from the precise torsion module 4 to the clamp and electrothermal coupling module 5, and the trajectory route of the test piece 28 in moving under the action of cantilever bending moment is simulated, thereby applying the cantilever bending load on the test piece 28;

Step 4: carrying out an indentation test nondestructive detection of the test piece 28 through a precise indentation module 8, where in operation, a rapid feed in horizontal and vertical directions is firstly performed by two ball screw drive units, then a first servo motor 44 drives a first screw 57 via a coupling 45 to move a mobile platform 47 to realize the precise feed, and finally, a flexible hinge 48 is driven by a piezoelectric ceramic 49 to push a weighing sensor 52 and a indenter 56 forward so as to press the indenter into the test piece, wherein the displacement distance of a second baffle 54 is measured by a displacement sensor 53, and the pressing depth can be measured indirectly, and wherein the methods of applying several individual loads can be combined to constitute a multi-load applying method, and the strain generated in the test piece 28 in the testing process can be obtained through a digital speckle measuring head 86;

Step 5: loading a hot field on the test piece 28 by applying different operating voltages to a silicon nitride ceramic heating sheet 32 in the clamp and electrothermal coupling module 5 and by heating the test piece 28 to different temperatures in a heat conductive manner, wherein the temperature is measured by an infrared thermal imager 84;

Step 6: loading a cold field on the test piece 28 by replacing the silicon nitride ceramic heating sheet 32 for heating in loading the hot field with a Peltier patch to refrigerate the test piece 28 to different temperatures, wherein the temperature is measured by the infrared thermal imager 84;

Step 7: loading an electric field on the test piece 28 in a manner of loading a large current, wherein the electric field is loaded by connecting the wire to a cable copper nose 41 and outputting a large current, and wherein the material performance detection test under the multi-load and multi-physical field test conditions is realized by combining the loading of the multi physical fields and the loading of multi loads.

Figure 9:
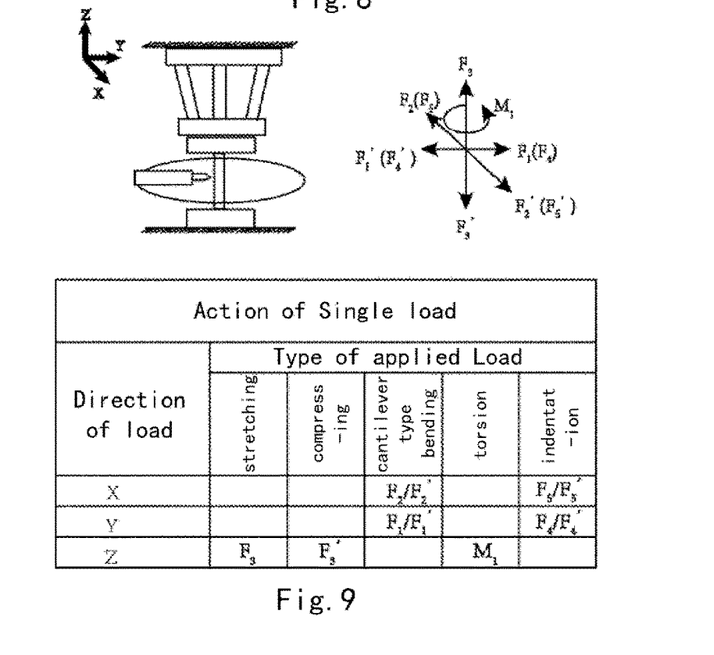
FIG. 9 is a schematic view showing the principle of applying an individual load according to the present disclosure.

Referring to FIGS. 8 to 13, the formula for the individual load applying according to the present disclosure is shown as follows:

I. the formula for calculating the stress under the Z-direction tension conditions:

$$\sigma = \frac{F_3}{A},$$

where $F_3$ is the Z-direction tensile force, A is the cross-sectional area of the test piece, the formula for calculating the strain ε under the Z-direction tension condition:

$$\varepsilon = \frac{\Delta l}{l},$$

where $\Delta l$ is the tension quantity of the test piece, l is the original length of the test piece;

II. the formula for calculating the stress σ under the Z-direction compression conditions:

$$\sigma = \frac{F'_3}{A},$$

where $F'_3$ is the Z-direction compression force;

the formula for calculating the strain ε under the Z-direction compression conditions:

$$\varepsilon = \frac{\Delta l}{l},$$

where $\Delta l$ is the compression quantity of the test piece;

III. the formula for calculating the maximum shear stress $\tau_{max}$ under the Z-direction torsion conditions:

$$\tau_{max} = \frac{M_1}{W_p},$$

where $M_1$ is the Z-direction torque and $W_p$ is the anti-torsion cross-section coefficient;

$$W_p = \frac{\pi D^3}{16},$$

where D is the diameter of the standard distance portion of the test piece;

the formula for calculating the torsion angle φ under the Z-direction torsion conditions;

$$\varphi = \frac{M_1 l}{G I_p},$$

where G is the shear modulus and $I_p$ is the polar moment of inertia of the section;

$$I_p = \frac{\pi D^4}{32};$$

IV. the formula for calculating the maximum stress $\sigma_{max}$ under the X(Y)-direction cantilever bending conditions:

$$\sigma_{max} = \frac{F_2 l}{W_Y},$$

where $F_2$ is the cantilever bending force in X direction, and $W_Y$ is the anti-bending section coefficient;

$$W_Y = \frac{\pi D^3}{32},$$

the formula for calculating the rotating angle $\theta_E$ of the movable end of the test piece under the X(Y)-direction cantilever bending conditions:

$$\theta_B = l \frac{F_2 l^2}{2EI},$$

where E is the elastic modulus, and I is the moment of inertia;

the formula for calculating the maximum deflection $f_E$ under the X(Y)-direction cantilever bending conditions:

$$f_B = l \frac{F_2 l^3}{2EI};$$

V. the formula for calculating the hardness H of the measured material in the X(Y)-direction indentation test:

$$H = \frac{P}{S},$$

where P is the real-time load corresponding to a certain indentation depth, and S is the projection area of the contact region between the indenter and the test piece material at this moment;

the formula for calculating the projection area of the typical indenter:
Berkovich indenter:
cubic corner indenter:
Vickers indenter:
tapered indenter: S=πa²,
spherical indenter: S=πa², where is the pressing depth, and a is the radius of the contact circle;

the formula for calculating the elastic modulus $E_z$ of the measured material in the X(Y)-direction indentation test:

$$E_s = \frac{1 - v_s^2}{1/E_r - (1 - v_i^2)/E_i},$$

where $E_z$ is the elastic modulus of the test piece, $E_r$ is the reduction modulus, $v_s$ is the Poisson's ratio of the test piece, $E_i$ is the elastic modulus of the diamond indenter (1050 GPa), $v_i$ is the Poisson's ratio of the diamond indenter (0.07).

Figure 10:
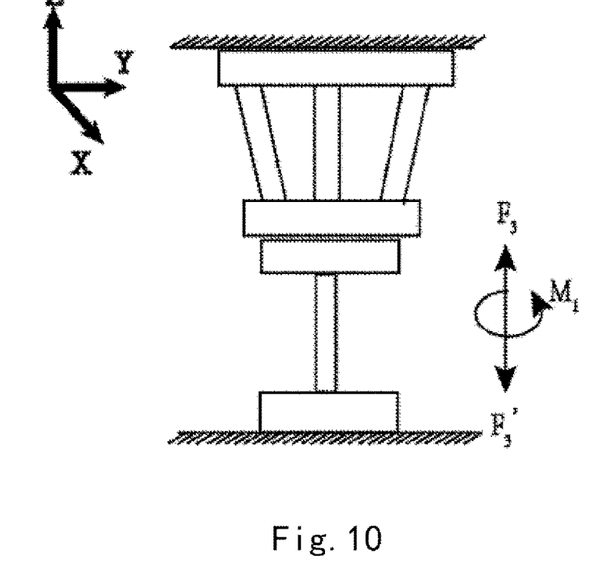
FIG. 10 is a schematic view showing the principle of loading a cantilever type tension/compression-torsion composite load according to the present disclosure.

The cantilever type tension/compression-torsion composite load according to the present disclosure is calculated as follows:

With the tension/compression-torsion composite load, each point on the entire circumferential surface of the test piece is a dangerous point, and according to the third strength theory, the formula for calculating the stress $\sigma_{r3}$ corresponding to the dangerous point is:

$$\sigma_{r3} = \sqrt{\sigma^2 + 4\tau^2} = \sqrt{\left(\frac{F_3}{A}\right)^2 + 4\left(\frac{M_1}{W_p}\right)^2},$$

where $F_3$ is the axial tensile force, A is the cross-sectional area of the test piece, $M_1$ is the torque, and $W_p$ is the anti-torsion cross-section coefficient.

According to the fourth strength theory, the formula for calculating the stress $\sigma_{r4}$ corresponding to the dangerous point is:

$$\sigma_{r4} = \sqrt{\sigma^2 + 3\tau^2} = \sqrt{\left(\frac{F_3}{A}\right)^2 + 3\left(\frac{M_1}{W_p}\right)^2}.$$

Figure 11:
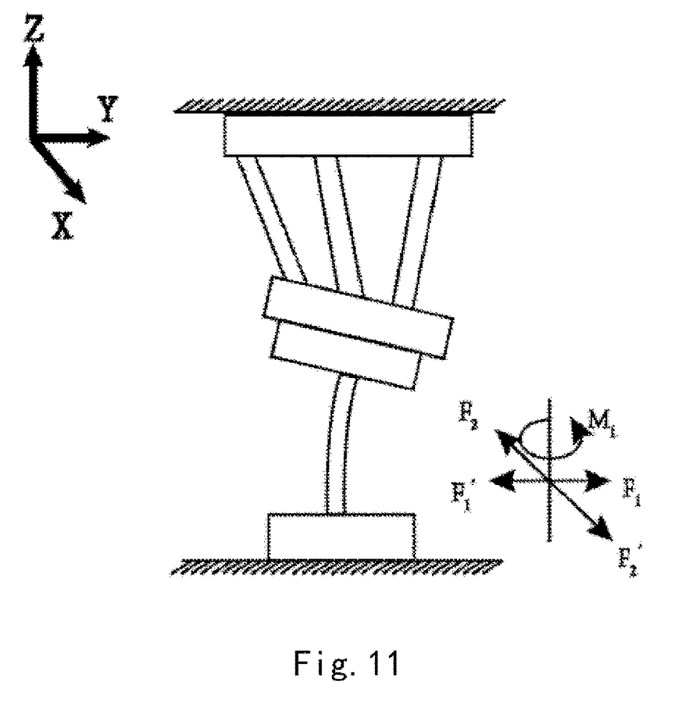
FIG. 11 is a schematic view showing the principle of loading a cantilever type bending-torsion composite load according to the present disclosure.

In the case of loading cantilever type bending-torsion composite load, the two edge points in the cross section of the fixed end of the test piece farthest from the neutral axis are the dangerous points. According to the third strength theory, the formula for calculating the stress $\sigma_{r3}$ corresponding to the dangerous point is:

$$\sigma_{r3} = \sqrt{\sigma^2 + 4\tau^2} = \frac{1}{W}\sqrt{M^2 + M_1^2},$$

where M is the cantilever bending moment, and W is the anti-bending section coefficient, $M_1$ is the torque.

According to the fourth strength theory, the formula for calculating the stress $\sigma_{r4}$ corresponding to the dangerous point is:

$$\sigma_{r4} = \sqrt{\sigma^2 + 3\tau^2} = \frac{1}{W}\sqrt{M^2 + 0.75 M_1^2}.$$

Figure 12:
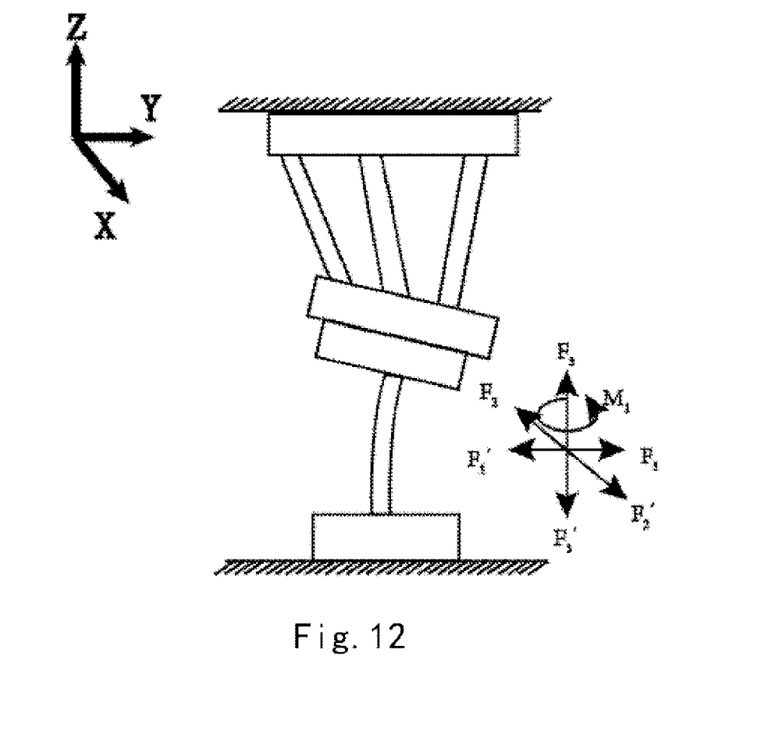
FIG. 12 is a schematic view showing the principle of loading a cantilever type tension/compression-bending-torsion composite load according to the present disclosure.

The cantilever type tension/compression-bending-torsion composite load according to the present disclosure is calculated as follows:

With the tension/compression-bending-torsional composite load, the two edge points in the cross section of the fixed end of the test piece farthest from the neutral axis are the dangerous points. According to the third strength theory, the formula for calculating the stress $\sigma^{r3}$ corresponding to the dangerous point is:

$$\sigma_{r2} = \sqrt{\sigma^2 + 4\tau^2} = \sqrt{\left(\frac{M}{W} + \frac{F_3}{A}\right)^2 + 4\left(\frac{M_1}{W_p}\right)^2}$$

where M is the cantilever bending moment, W is the anti-bending section coefficient, $F_3$ is the axial tensile force, A is the cross-sectional area of the test piece, $M_1$ is the torque, and $W_p$ is the anti-torsion cross-section coefficient.

Figure 13:
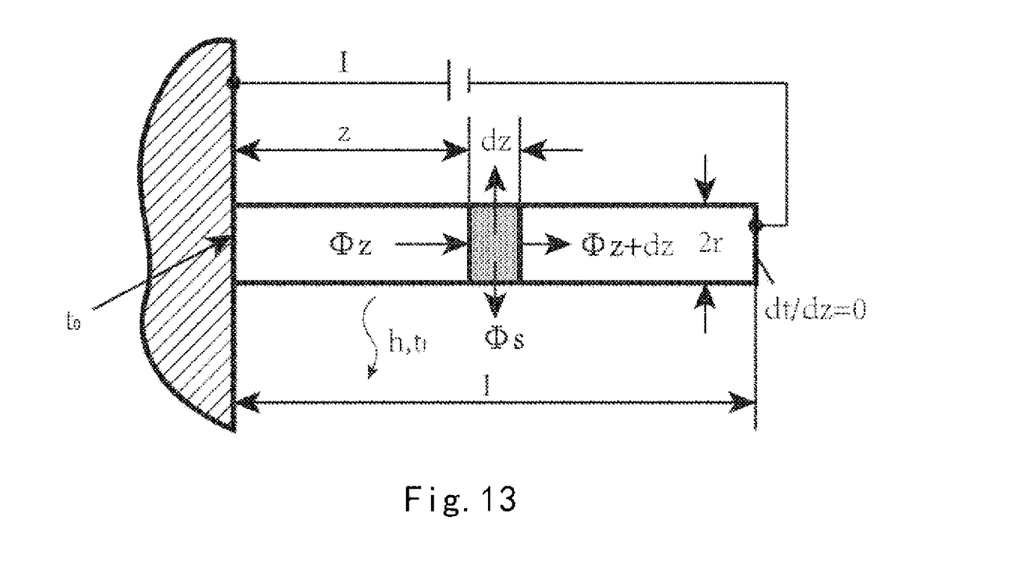
FIG. 13 is a schematic view showing the principle of loading the cold/hot-electric field composite physical field according to the present disclosure.

The cold/hot-electric field composite physical field according to the present disclosure can be analyzed and calculated as follows:

The test piece has a symmetric structure. One half of the test piece is taken as the analyzed object. The cold/hot-electric field compound loading is simplified as a heat conduction problem in which there is a constant property, a steady state, of one-dimension and an internal heat source. The differential equation of heat conduction is shown as:

$$\frac{\partial^2 t}{\partial z^2} + \frac{\Phi}{\lambda} = 0$$

where t is the temperature of the test piece, $\lambda$ is the thermal conductivity of the test piece, $\dot{\Phi}$ is quantity of heat generated by the inner heat source per unit volume per unit time. In this case, the quantity of the heat $\dot{\Phi}_s$ generated by air heat convection on the outer surface of the test piece and the quantity of the Joule heat $\dot{Q}$ generated by energizing the test piece can be converted into that of the inner heat source. That is, $$\dot{\Phi} = \dot{\Phi}_s + \dot{Q}.$$

A micro-segment of the test piece with a length of dz is taken as an object to be analyzed. The quantity of the heat generated by heat convection is shown as:

$$\dot{\Phi}_s = \frac{h(t - t_f)2\pi r dz}{\pi r^2 dz},$$

where is the convection heat transfer surface heat transfer coefficient, $t_f$ is the temperature of the air, r is the radius of the test piece.

A micro-segment of the test piece with a length of dz is taken as an object to be analyzed. The quantity of the Joule heat generated by energizing the test piece heat $\dot{Q}$ is:

$$\dot{Q} = \frac{I^2 \rho \frac{dz}{\pi r^2}}{\pi r^2 dz}$$

where l is the current passing through the test piece, and $\rho$ is the resistivity of the test piece.

The two corresponding boundary conditions are shown as:

$$z = 0, t = t_0; z = l, \frac{dt}{dz} = 0.$$

The disclosure is mainly developed for material microproperties in-situ test under multi-load and multi-physical field coupling. In addition to the individual loading method of the conventional four types of loads, i.e. "tension/compression-torsion-bending-indentation", the loading of a composite load can also be achieved, such as novel loading methods of "cantilever type pure bending, cantilever type tension/compression-torsion, cantilever type bending-torsion, and cantilever type tension/compression-bending-torsion". By simultaneously coupling multi-physical fields, such as the temperature field and the electric field, the functional material testing under a "composite load and multi-physical field" coupling the that cannot be realized by the traditional test instruments can be achieved. The device according to the disclosure is integrated with a continuous zoom microscope, which can realize the dynamic tracing in the experiment process. The deformation behavior, damage mechanism and evolution rule of the material under the new loading mode can be dynamically monitored. At the same time, the device according to the disclosure is also integrated with a non-contact optical strain measuring instrument. By means of the use of this technology, a detailed explanation report on the strain distribution of the various parts of the material can be made after the test ends, and the dynamic change of the stress and the strain in the process of testing can be exhibited in the form of videos.

The foregoing description merely gives exemplified embodiments of the present disclosure and is not intended to limit the present application. Various changes and modifications may be made by those skilled in the art. Any modifications, equivalents, improvements, and the like to the present disclosure should fall within the scope of the present disclosure.

What is claimed is:

1. A material in-situ test device under multi-load and multi-physical field coupled service conditions, in which a vertical asymmetric arrangement with three columns is adopted, comprising a support frame module, a shock isolation platform, a precise six-degree-of-freedom composite load applying module, a precise torsion module, a clamp and electrothermal coupling module, a digital speckle strain measurement and infrared thermal imaging module, an in-situ observation module, a precise indentation module and a circumferential positioning module, wherein the precise six-degree-of-freedom composite load applying module is connected to the support frame module by a stationary platform, and tension/compression and bending loads are applied on a test piece by means of the cooperation action of six electric cylinders, wherein the precise torsion module is provided on a movable platform of the precise six-degree-of-freedom composite load applying module, wherein the clamp and electrothermal coupling module is connected to the precise torsion module via a flange, wherein the digital speckle strain measurement and infrared thermal imaging module is provided on the shock isolation platform through an adjustable support base, wherein the in-situ observation module and the precise indentation module are provided on the circumferential positioning module to realize a rotatable in-situ observation on the test piece.

2. The material in-situ test device under multi-load and multi-physical field coupled service conditions according to claim 1,
wherein the precise six-degree-of-freedom composite load applying module comprises a movable platform, a Hooke hinge, a motor, a decelerator, an electric cylinder and a stationary platform,
wherein the stationary platform is fixedly connected to the support frame module,
wherein one end of each electric cylinder is connected to the movable platform through the Hooke hinge and the other end is connected to the stationary platform,
wherein the motor and the decelerator are connected to the stationary platform, respectively, and
wherein under the cooperation action of the six electric cylinders, a flexible movement in six degree of freedom directions is achieved.

3. The material in-situ test device under multi-load and multi-physical field coupled service conditions according to claim 1,
wherein a torsional feed in the precise torsion module is provided by a DC servo drive motor and a planetary gear reducer, and a first thrust bearing and a second thrust bearing are mounted on a spline shaft to counteract an axial load generated on the DC servo drive motor and the planetary gear reducer when a tension/compression load is applied; and
wherein the spline shaft transmits the torque to the flange by a spline; the shaft end of the spline shaft is bolted to the flange and transmits the axial tension/compression force.

4. The material in-situ test device under multi-load and multi-physical field coupled service conditions according to claim 1,
wherein the clamp and electrothermal coupling module is connected to a six-dimensional force sensor by means of two double end studs,
wherein the test piece is clamped by tightening a pre-load bolt to produce a downward compression force to compress a cover plate and a first baffle, and
wherein the test piece is tightly pressed by means of the friction force via a groove in the clamp that matches the test piece in shape.

5. The material in-situ test device under multi-load and multi-physical field coupled service conditions according to claim 1,
wherein the clamp and electrothermal coupling module integrates the clamp with the function of loading the cold, hot and electric multi-physical fields,
wherein the loading of the hot field is achieved by energizing a silicon nitride ceramic heating sheet provided in the clamp in advance to load the heat field,
wherein the loading of the cold field is achieved by replacing the silicon nitride ceramic heating sheet with a Peltier patch and energizing the Peltier patch, thereby realizing the refrigerating, and
wherein the loading of the electric field is achieved by connecting a wire to a cable copper nose and loading a current.

6. The material in-situ test device under multi-load and multi-physical field coupled service conditions according to claim 1,
wherein in the digital speckle strain measurement and infrared thermal imaging module, a digital speckle measuring head is provided on the shock isolation platform through an adjustable support base,
wherein an infrared thermal imager is fixed to a support base, and the support base is fixed to the adjustable support base,
wherein the position of the adjustable support base relative to the test piece is adjustable to meet the desired parameter requirements for the operation of the digital speckle measuring head.

7. The material in-situ test device under multi-load and multi-physical field coupled service conditions according to claim 1,
wherein the in-situ observation module is entirely fixed to an observation platform, and the observation platform is circumferentially rotated about the test piece,
wherein the observation platform is driven by a servo motor and a speed reducer that drive a roller to rotate, and the roller engages with a circular ring gear to achieve a circumferential feed, and
wherein the whole observation platform is fixed to a slider, thereby realizing a circumferential motion.

8. The material in-situ test device under multi-load and multi-physical field coupled service conditions according to claim 7,
wherein the radial and axial rapid feed of the in-situ observation module around the circular ring gear is realized by a stepping motor and a servo motor, respectively,
wherein a microscope is rapidly moved into an observation area, and then the microscope is automatically focused,
wherein after the focus is adjusted as desired, the observation is carried out.

9. The material in-situ test device under multi-load and multi-physical field coupled service conditions according to claim 1,
wherein the radial and axial rapid feed of the in-situ observation module around the circular ring gear is realized by a stepping motor and a servo motor, respectively,
wherein a microscope is rapidly moved into an observation area, and then the microscope is automatically focused,
wherein after the focus is adjusted as desired, the observation is carried out.

10. The material in-situ test device under multi-load and multi-physical field coupled service conditions according to claim 1,
wherein the precise indentation module is fixed to the circumferential positioning module,
wherein when the precise indentation module operates, the radial and axial rapid feed of the precise indentation module around a circular ring gear is carried out by two ball screw drive units, and
wherein after the positioning is completed, a flexible hinge is driven by means of a piezoelectric ceramic to produce a forward displacement, pressing an indenter into the test piece.

11. A material in-situ testing method under multi-load and multi-physical field coupled service conditions, comprising the following steps:
Step 1: applying a tension/compression load borne by a test piece by means of a precise six-degree-of-freedom composite load applying module, wherein six electric cylinders are driven to elongate or shorten by corresponding motors and corresponding decelerators that are connected to a stationary platform, the load is transferred from a movable platform to a precise torsion module and then from the precise torsion module to a clamp and electrothermal coupling module, thereby applying the tension/compression load on the test piece;

Step 2: applying a torsion load borne by the test piece by means of the precise torsion module, wherein a DC servo drive motor and a planetary gear reducer drive a spline shaft to rotate, and the spline shaft drives a sensor flange, a flange and a six-dimensional force sensor to rotate, thereby rotating the upper end of a clamp and electrothermal coupling module and applying of the torsion load on the test piece with the lower end of the clamp and electrothermal coupling module being fixed;

Step 3: applying a cantilever bending load borne by the test piece by means of the precise six-degree-of-freedom composite load applying module, wherein the six electric cylinders are driven to elongate or shorten to different extents by the motor and the decelerator that are connected to the stationary platform, the load is transferred from the movable platform to the precise torsion module and then from the precise torsion module to the clamp and electrothermal coupling module, and the trajectory route of the test piece in moving under the action of cantilever bending moment is simulated, thereby applying the cantilever bending load on the test piece;

Step 4: carrying out an indentation test or nondestructive detection of the test piece through a precise indentation module, where in operation, a rapid feed in horizontal and vertical directions is firstly performed by two ball screw drive units, then a first servo motor drives a first screw via a coupling to move a mobile platform to realize the precise feed and finally, a flexible hinge is driven by a piezoelectric ceramic to push a weighing sensor and an indenter forward so as to press the indenter into the test piece, wherein the displacement distance of a baffle is measured by a displacement sensor, and the pressing depth is measured indirectly, and wherein a plurality of types of loads are applied in combination to constitute a multi-load applying mode, and the strain generated in the test piece in the testing process can be obtained through a digital speckle measuring head;

Step 5: loading a hot field on the test piece by applying different operating voltages to a silicon nitride ceramic heating sheet in the clamp and electrothermal coupling module and by heating the test piece to different temperatures in a heat conductive manner, wherein the temperature is measured by an infrared thermal imager;

Step 6: loading a cold field on the test piece by replacing the silicon nitride ceramic heating sheet for heating in loading the hot field with a Peltier patch to refrigerate the test piece to different temperatures, wherein the temperature is measured by the infrared thermal imager;

Step 7: loading an electric field on the test piece in a manner of loading a large current, wherein the electric field is loaded by connecting the wire to a cable copper nose and outputting a large current, and wherein a material performance detection test under the multi-load and multi-physical field test conditions is realized by combining the loading of the multi physical fields and the loading of multi loads.

* * * * *